United States Patent [19]
Shaw

[11] Patent Number: 5,960,794
[45] Date of Patent: Oct. 5, 1999

[54] SURGICAL DRAPE

[76] Inventor: Timothy A. Shaw, P.O. Box 129, Payson, Ariz. 85547

[21] Appl. No.: 08/964,511

[22] Filed: Nov. 5, 1997

[51] Int. Cl.$^6$ .................................................. A61B 19/00
[52] U.S. Cl. ........................................... 128/849; 128/853
[58] Field of Search ..................................... 128/849–856

[56] References Cited

U.S. PATENT DOCUMENTS

| | | | |
|---|---|---|---|
| 2,662,525 | 12/1953 | Priebe | 128/283 |
| 2,688,327 | 9/1954 | Berg | 128/283 |
| 2,778,362 | 1/1957 | Pollock et al. | 128/283 |
| 2,788,785 | 4/1957 | Present | 128/283 |
| 4,275,719 | 6/1981 | Mayer | 128/849 |
| 4,462,396 | 7/1984 | Wichman | 128/132 D |
| 4,598,458 | 7/1986 | McAllester | 128/853 |
| 4,681,574 | 7/1987 | Eastman | 604/344 |
| 4,834,711 | 5/1989 | Greenfield | 604/172 |
| 4,905,710 | 3/1990 | Jones | 128/853 |
| 5,026,362 | 6/1991 | Willett | 604/345 |
| 5,125,916 | 6/1992 | Panebianco et al. | 604/332 |
| 5,388,593 | 2/1995 | Thomalla | 128/853 |

*Primary Examiner*—Michael A. Brown
*Attorney, Agent, or Firm*—Schmeiser, Olsen & Watts

[57] ABSTRACT

A surgical barrier used on a patient during an operating procedure. Wherein the barrier includes a drape, having a patient and doctor side; and valve, located on the drape, for maintaining a barrier between the patient and doctor side while a surgical instrument extends therethrough. The surgical barrier also has a reservoir, located adjacent the valve, for holding a solution therein. Additionally, the reservoir includes a pore for expelling the solution onto the surgical instrument located on the patient side. Moreover, the reservoir includes a refill device for refilling the reservoir with solution. The reservoir has a hollow walled ring shape that is formed circumfrentially around the valve. The hollow walled ring defines a cavity therebetween. The valve is specifically located within the cavity adjacent the doctor side of the drape. Additionally, the surgical barrier includes a collection bag, located on the patient side of the drape, for collecting secretions from a patient during an operating procedure. The surgical barrier also includes on an adhesive tape located on a periphery of the drape.

19 Claims, 3 Drawing Sheets

SURGICAL DRAPE

BACKGROUND OF THE INVENTION

1. Field of the Invention

The present invention generally relates to an a surgical drape used in performing a colonoscopy. Specifically, there is a colonoscopy drape that prevents secretions or aerosolization from being expelled onto the side of the drape near the physician and technicians during a colonoscopy procedure.

2. Description of Related Art

The intestine is a major part of the digestive tract. The intestine extends from the exit of the stomach to the anus. The overall shape forms a long tube divided into two main sections, the small intestine and the large intestine. The function of the intestine is to break down and absorb food and water into the bloodstream and carry away the waste products of digestion to be passed as feces.

The small intestine is about twenty one feet in length and one and one-half inches in diameter. It has three sections- the duodenum (a short, curved segment fixed to the back wall of the abdomen) and the jejunum and ileum (two larger, coiled, and mobile segments). The bile and pancreatic ducts enter the duodenum.

The walls of the intestine consist of circular and longitudinal muscles with an internal lining (the mucosa) and an external covering (the serosa). Peristalsis (the rhythmic contraction of the muscles) forces partially digested food along the intestine. The mucosa consists of many villi (small, finger-like projections) covered with millions of fronds that create a large surface area to help the absorption of substances into the blood.

The small intestine is concerned with the digestion of food and the absorption of food into the bloodstream. Some digestion occurs in the stomach, but more digestive enzymes and bile are added to the partly digested food in the duodenum. Glands within the walls of each section of the small intestine produce mucus and more enzymes, all of which help to break down the food into easily absorbable chemical units. The numerous blood vessels in the intestinal walls then carry the digested food to the liver for distribution to the rest of the body.

The large intestine is about six feet in length and two inches in diameter; it frames the loops of the small intestine. Unlike the small intestine, much of it is fixed in position, the muscles run in bands rather than forming a continuous sheet along its length.

The major part of the large intestine is the colon. The colon is a segmented tube about two and one-half inches wide and four and one-half feet long. Its segments, or haustrations, give it an irregular outline.

The colon consists of four sections: the ascending, transverse, descending, and sigmoid colon. The first part, the ascending colon, starts at the cecum, in the lower right-hand side of the abdomen, and extends up to a sharp bend just below the liver. This point, called the hepatic flexure, marks the beginning of the transverse colon, which loops across the abdomen, passing below the stomach to the spleen on the left-hand side of the abdomen. Here, there is a shape downward bend (called the splenic flexure) that marks the start of the descending colon. From this point, the descending colon passed down the left side to approximately the brim of the pelvis, where it adopts an S-shaped course of variable length (the sigmoid colon) to connect with the rectum at the lower left-hand side of the abdomen.

The colon is muscular tube with a lubricated inner lining. Its outermost layer, called the serous coat, is a tough, fibrous membrane with a smooth outer surface. This membrane protects the colon from damage when intestinal movements cause it to rub against the abdominal wall.

The muscular coat consists of three bands of longitudinal muscles and an inner layer of circular muscles. Peristalsis squeezes the intestinal contents through the colon.

Inside the muscular coat is the third layer, the submucous coat. It consists of connective tissue, blood vessels, and lymphatic vessels.

The innermost layer is the mucous coat, which contains numerous tubular glands. These glands produce large amount of mucus to lubricate the passage of digested material through the colon. Unlike the small intestine, the mucous coat of the colon (and the rest of the large intestine) is not folded into villi (tiny, finger-like projections).

The functions of the colon are, principally, to absorb water (and also a small amount of mineral salts) from the digested material passing through the colon and to concentrate indigestible waste for expulsion as feces.

When the intestinal contents enter the colon, digestion has been completed and the material is in the form of a liquid. As this liquid passes through the colon, the water and salts it contains are absorbed into the blood vessels in the submucous coat. By the time the intestinal contents pass out of the colon into the rectum, almost all the water has been absorbed and the contents are in the form of feces.

Disorders of the Intestine

The intestine is subject to various structural abnormalities and to the effects of many infective organisms and parasites; it may also be affected by tumors, impaired blood supply, and other disorders.

Tumors of the large intestine are very common. Certain forms of familial polyposis (a disorder in which benigh polyp-like tumors grow in the colon) may progress to cancer.

Like other organs, the intestine is dependent on an adequate blood supply. Ischemia (lack of blood) may result from several causes. Causes include partial or complete obstruction of the arteries in the abdominal wall (from disease such as atherosclerosis, thrombosis, or embolism) or from the blood vessels being compressed or trapped, as in volvulus, intussusception, or hermias (protrusion of intestines through the abdominal wall). Loss of blood supply to a segment of intestine may cause gangrene (tissue death) requiring immediate surgery.

Intestinal obstruction may be caused by pressure from the outside, disease of the intestinal wall (such as cancer, Crohn's disease, or diverticular disease), or internal blockage (such as from gallstones or intussusception). One of the most common causes is paralytic ileus, in which intestinal contractions cease and the intestinal contents are no longer transported.

Peptic ulcer of the duodenum is a very common disorder, thought to affect 10 percent of the population. Ulceration of the small intestine occurs in typhoid and Crohn's disease and may cause bleeding into the intestine or even perforation (hole formation). Ulceration of the large intestine occurs in amebiasis and in ulcerative colitis.

Diverticula are small outpouchings from the inside of the bowel. They are usually harmless, but in diverticular disease, become inflamed. Malabsorption and celiac aprue result from changes to the intestinal lining. Finally, irritable bowel syndrome is associated with persistent abdominal pain and either constipation or diarrhea and is the most common intestinal disorder in Western societies.

Intestinal disorders are investigated by physical examination and by techniques such as barium X-ray examination, signoidoscopy, or possibly colonoscopy, and by laboratory examination of the feces or of a biopsy specimen taken from the intestinal lining.

Colonoloscopy

Colonoscopy is an examination of the inside of the colon by means of a long, flexible, fiberoptic viewing instrument called a colonoscope. Colonoscopy is used to investigate symptoms, such as bleeding from the bowel, and to look for disorders of the colon. Attachments at the end of the instrument enable the physician to take biopsy specimens or brushings for cytologic examination and to remove polyps.

The patient takes laxatives for one or two days before the examination to empty the colon of feces. Because the procedure causes a little discomfort, the patient is lightly sedated beforehand. The colonoscope is passed into the colon through the anus and guided along the length of the colon, which the operator examines through a viewing lens. A complete examination of the entire colon can take from ten minutes to a couple of hours to perform.

Related Patents

Examples of patents that are related to the present embodiment of colonoscopy procedures are as follows, wherein each of the following patents are herein incorporated by reference for the supporting teachings:

U.S. Pat. No. 5,125,916, is an ostomy appliance that is for selectively sealing a stoma. The appliance includes a central elongated relatively rigid tube having inner and outer end portions. A cap is support to the outer end portion of the tube and is adapted to engage the users skin when the tube is inserted in a stoma. A flexible extendable and collapsible bellows is mounted on the inner end of the tube for sealing the inside of the stoma when the appliance is inserted therein. A flexible rod is insertable through the cap and tube for engagement with the bellows.

U.S. Pat. No. 5,026,362, is an ostomy bag holder and cover of lightweight fabric material, comprising a waist encircling belt adapted to be adjustably secured about the waist of the user, and a pouch secured to the belt for holding and covering an ostomy bag. The pouch has a back panel having a cut-out therein for proofing access from an ostomy bat to a stoma, and a front panel having releasable fastening means thereon for releasably attaching the front panel to the belt for covering an ostomy bag supported in the pouch. The front and back panels define a pocket at their lower ends for supporting the ostomy bag.

U.S. Pat. No. 4,681,574, is an ostomy appliance in which an ostomy bag is supported on the user's skin by a membrane adhesively held on the skin where the membrane and adhesive layer are very thin, flexible, elastic and highly permeable to water vapor and oxygen transmission. A stiffening member is removably provided for mounting the very thin, flexible membrane in a spread out condition while it is being attached to the skin, and the stiffening member is thereafter removed so that the appliance is supported on the skin only by the flexible permeable membrane.

U.S. Pat. No. 4,462,396, is a surgical drape comprising, a main sheet of flexible material having an inner surface for facing a patient after placement of the drape, an outer surface for facing away from the patient after placement of the drape, and a fenestration. The drape has a pocket comprising a secondary sheet of flexible material having a pair of end edges, a pair of side edges connecting the end edges, a first surface and an opposing second surface. The secondary sheet has a first fold line extending between the end edges at a location between the died edges and defining a pair of first and second panels extending between the first fold line and the side edges. The first surface of the first and second panels face each other in the folded sheet. The first and second panels have second and third fold lines defining a pair of opposed first and second flaps and a central portion extending between the flaps. The second and third fold lines extend from the juncture of the end and side edges to the first fold line at a location spaced from the one edges. The flaps are folded against the first panel. The central portion defines a cavity communication with an opening defined by the side edges. The flaps are secured to the central portion, and the pocket is secured to the main sheet with the opening facing toward the expected path of fluid run-off from the fenestration.

U.S. Pat. No. 2,788,785, is a surgical belt which includes a band made from elastic webbing of suitable width, and provided on each of its end edges with portions of a separable fastener such as a slide fastener whereby the end edges may be connected together to extend about the body of a patient or wearer. While the band is of elastic webbing capable of elongation, for maximum comfort of the wearer the elongation and pressure imposed on the body by the band should be somewhat uniform. Therefore, inserts or sections of elastic webbing are arranged with portions of a wearable slide fastener suitably secured on each end respectively adapted to be engaged with the fastener portions respectively to adjust the belt to a suitable size to provide the proper fit around persons of different size. Different length or a plurality of sections may be used to give desired variation in the size of the band. It is preferable that the slide fasteners extend from the lower edges of the band and section upward therefrom and terminate as at with the portion of the ends of the band between the end of the slide fastener and their upper edge of the band being provided with hooks and eyes, the ends of the sections also being provided with corresponding mating hooks and eyes for connection thereto. The hook and eye or other suitable fasten arrangement is preferably used with the slide fastener so as to assure connection for substantially the full length of the ends of the band and sections. The edges and of the band are preferably covered by a suitable elastic binding secured thereto as by stitching to prevent the band from folding or curling up on the wearer. Loops of fabric are preferably secured in spaced relation to the band adjacent the lower edge for attachment of garters or other straps if desired. Also, the lower edge and upper edge of the band and sections may be of equal length or one shorter than the other to fit the body of the wearer; however, usually the upper edge is slightly shorter as it should extend substantially about the waist of the wearer.

U.S. Pat. No. 2,778,362, is a surgical garment which may be in the form of a girdle and which may have portions in the front formed of any suitable fabric. Further, at the sides or other portions as may be desired, the garment may be provided with elastic portions. A slide fastener closure is provided to permit the garment to be easily removed or replaced on the body of the user and to facilitate removal and replacement of disposable plastic bag.

U.S. Pat. No. 2,688,327 is a colostomy device and consists of an under-belt of elastic material to which a pocket containing a charcoal pad is fitted, and an overbelt giving abdominal support which is designed to be worn over the underbelt.

U.S. Pat. No. 2,662,525, is a colostomy pouch having sanitary comfort and cover to increase the comfort of the patient wearing the pouch.

These incorporated by reference patents reflect the state of the art of which the applicant is aware and are tendered with a view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

It is a feature of the invention to provide a surgical barrier used on a patient during an operating procedure. Wherein the barrier includes a drape, having a patient and doctor side; and valve, located on the drape, for maintaining a barrier between the patient and doctor side while a surgical instrument extends therethrough.

Another feature of the surgical barrier comprising a reservoir, located adjacent the valve, for holding a solution therein. Additionally, the reservoir includes a pore for expelling the solution onto the surgical instrument located on the patient side. Moreover, the reservoir includes a refill device for refilling the reservoir with solution. The reservoir has a hollow walled ring shape that is formed circumfrentially around the valve. The hollow walled ring defines a cavity therebetween. The valve is specifically located within the cavity adjacent the doctor side of the drape.

Yet a further feature of the surgical barrier includes a collection bag, located on the patient side of the drape, for collecting secretions from a patient during an operating procedure.

Still an additionally feature of the surgical barrier includes on an adhesive tape located on a periphery of the drape.

The invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

Further, the abstract is neither intended to define the invention of the application, which is measured by the claims, neither is it intended to be limiting as to the scope of the invention in any way.

Other features of the present invention will become more clear from the following detailed description of the invention, taken in conjunction with the accompanying drawings and claims, or may be learned by the practice of the invention.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention.

Charter by the U.S. Constitution

This disclosure of the invention is submitted in furtherance of the constitutional purposes of the United States Patent Laws "to promote the progress of science and useful arts," as stated in Article 1, section 8, clause 8 of the United States Constitution.

DETAILED DESCRIPTION OF THE PREFERRED EMBODIMENT

Figure 1:
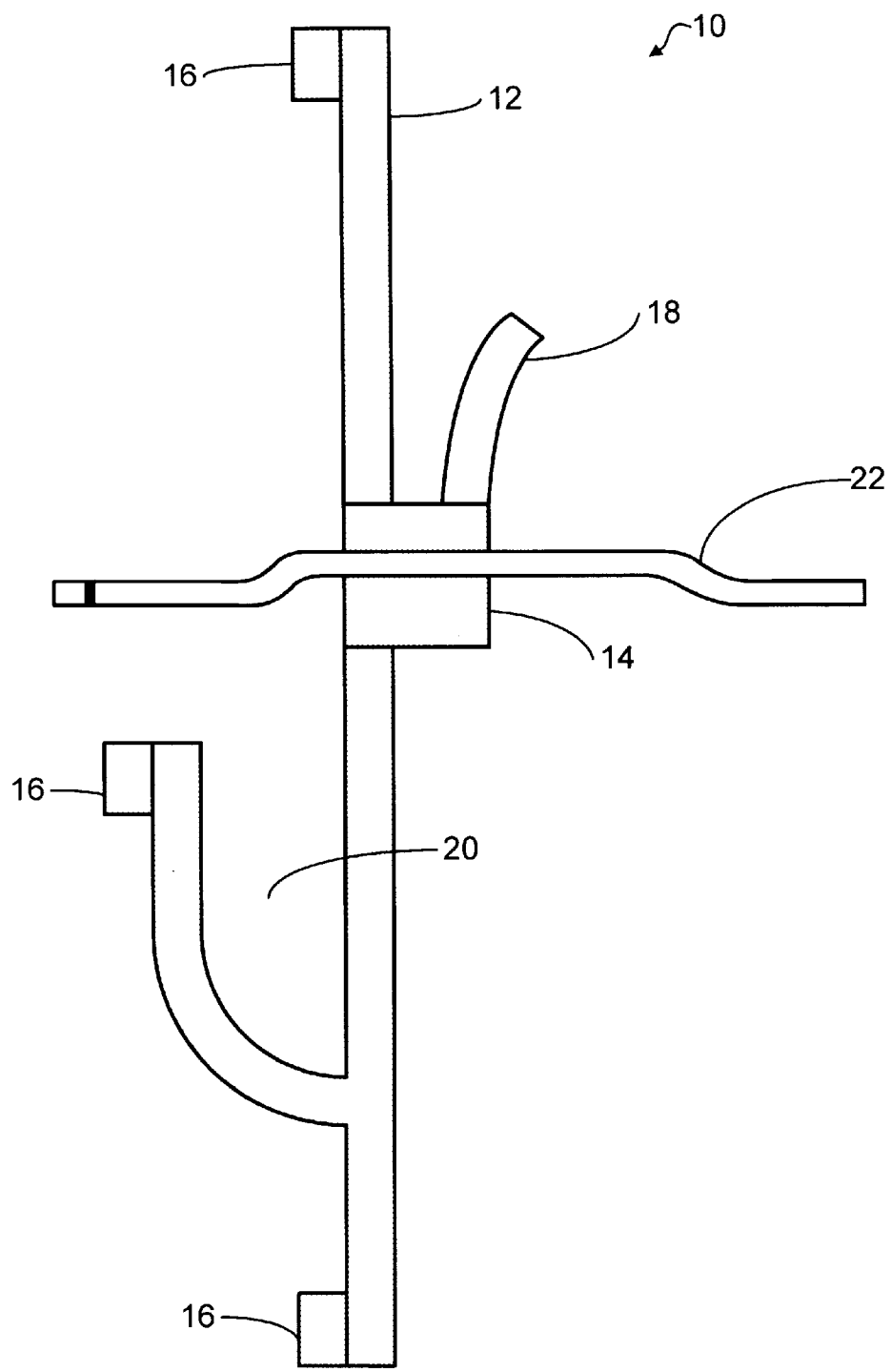
FIG. 1 is a cross sectional side view of the preferred embodiment.
Figure 2:
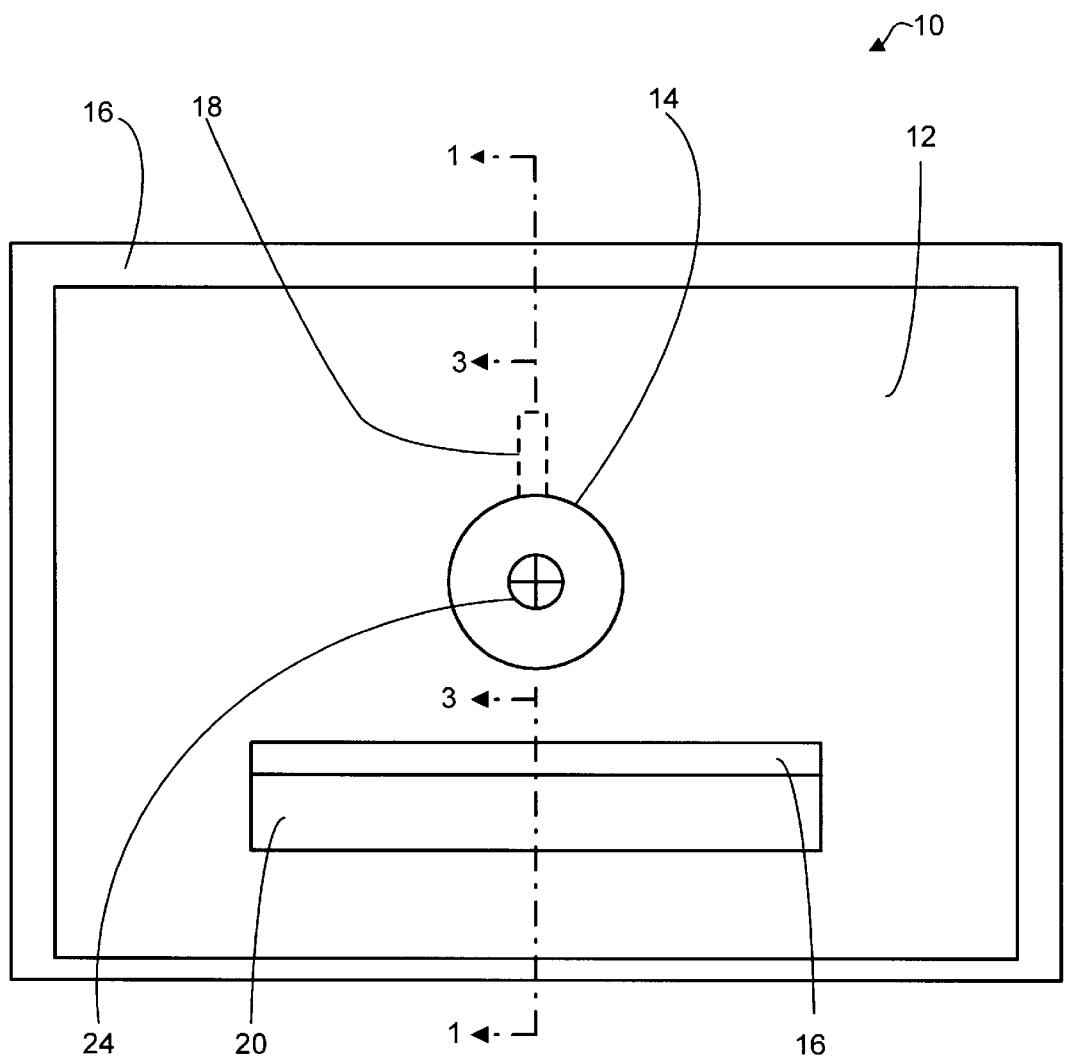
FIG. 2 is a top view of the preferred embodiment illustrated in FIG. 1.

Referring to both FIGS. 1 and 2, there is illustrated a cross sectional side view and a top view of the preferred embodiment respectively. Colonoscopy containment barrier 10 consists of a drape 12 material either cloth or preferably plastic. Barrier 10 has the periphery lined with adhesive material 16 capable of releasably attaching to a human body. A reservoir structure 14 is positioned in a central location of the drape 12, which includes a refill tube 18 for refilling the reservoir structure 14 with lubricant (not shown) and a valve 24 used to insert colonoscope 22 therethrough. Attached to the barrier 10 is a collection bag 20, used to collect secretions from a patient during the colonoscopy procedure.

Figure 3:
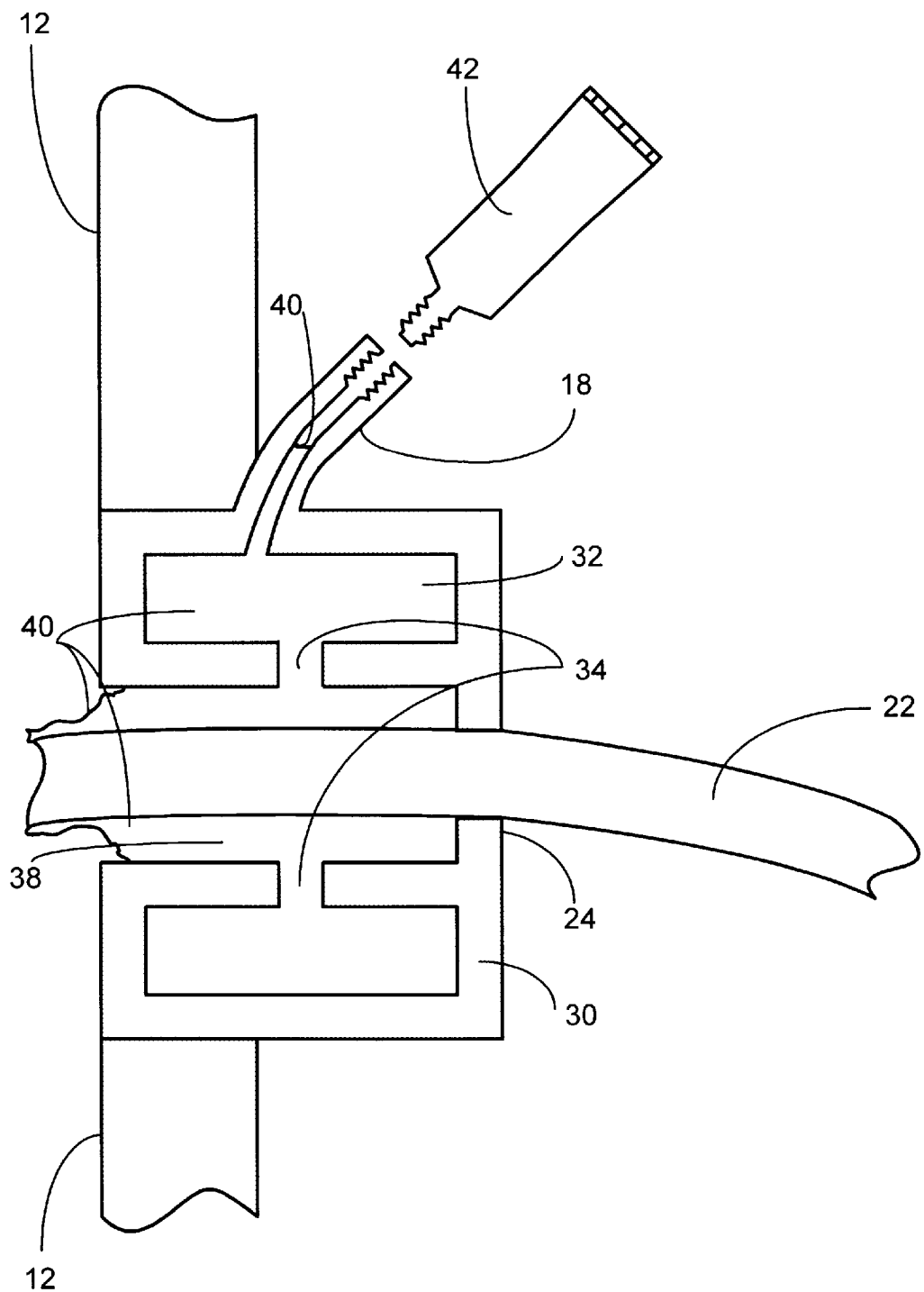
FIG. 3 is a cross sectional view of the valve assembly of the preferred embodiment illustrated in the previous figures.

FIG. 3 illustrates a sectional view of the reservoir structure 14 shown in the previous figures. Reservoir structure 14 includes a wall 30 that defines reservoir 32, which contains lubricating solution 40. Refill tube 18 has a threaded mouth 36 for threading a lubricant tube 42 thereto for refilling reservoir 32. Wall 30 has pores 34 for filling chamber 38 with lubricant 40, which is used for coating colonoscope 22 as it passes through valve 24 and chamber 38.

One skilled in the art will easily appreciate the operation of the preferred embodiment. The adhesive tape 16 will adhere to a patient to create an effective barrier to protect the doctor and support staff from aerosolization and secretions during a colonoscopy procedure. The positioning of the collection bag serves to effectively collect most all secretions occurring during the procedure. The lubricant 40 is stored in the reservoir 32 and squeezed out of the pores 34 to fill the chamber 38 with lubricant 40 before the colonoscope 22 is inserted therethrough. Of course the mouth 36 of the tube 18 must be plugged during the filling of the chamber; this is done by leaving the tube 42 thereon or by placing a plug or cap thereon.

Variations in the Preferred Embodiment

Although this embodiment focuses upon the application of the barrier 10 for a colonoscopy procedure, one skilled in the art will realize that the barrier 10 may be used for any type of operation that would benefit from creating a barrier between the patent and the doctor. For example, it is contemplated to use the barrier 10 in the application of a barium enema that is used in several x-ray procedures.

The current embodiment illustrates the use of a short tube 18. However, it may be found that a longer tube 18 would be more efficient.

Additionally, a single valved 24 reservoir 14 is illustrated. It is contemplated to modify this design with using a valve at either end of the chamber 38.

One skilled in the art will also realize that the positioning of the various pores 34 located in the reservoir structure 14 walls 30 is variable. The pores 34 could be positioned near the bottom or top, and there could be many or few pores therein.

The design of the reservoir structure 14 is shown as a square-shaped donut. Where in fact, the reservoir structure 14 may be most any shape that allows an inserted colonoscope 22 to be coated with lubricant 40. Additionally, the size of the reservoir 32 may be relatively much smaller or larger. If smaller, the lubricant tube 42 would act as the larger reservoir and the current reservoir 32 would act more like the tube 18 (used to route the lubricant to the chamber 38).

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A surgical barrier used on a patient, comprising:
   a) a drape, having a patient and doctor side;
   b) a valve, located on the drape, for maintaining a barrier between the patient and doctor side while a surgical instrument extends therethrough;
   c) a collection bag attached to the drape for collecting secretions from a patient during a surgical procedure; and
   d) reservoir means, located adjacent the valve means, for holding a solution therein.

2. The surgical barrier of claim 1, wherein the reservoir means includes a pore for expelling the solution onto the surgical instrument located on the patient side.

3. The surgical barrier of claim 1, wherein the reservoir means includes a refill means for refilling the reservoir with solution.

4. The surgical barrier of claim 1, wherein the reservoir has a hollow walled ring shape that is formed circumfrentially around the valve means.

5. The surgical barrier of claim 4, wherein the hollow walled ring defines a cavity therebetween.

6. The surgical barrier of claim 5, wherein the valve means is located within the cavity adjacent the doctor side.

7. The surgical barrier of claim 6, wherein the cavity includes a pore for expelling the solution onto the surgical instrument located within the cavity.

8. The surgical barrier of claim 1, wherein the collection bag further comprises an adhesive portion capable of releasably attaching to a patient.

9. The surgical barrier of claim 8, wherein a periphery of the drape includes an adhesive portion capable of releasably attaching to a patient.

10. A surgical barrier used on a patient, comprising:
    a) a drape, having a patient and doctor side;
    b) a reservoir means, located on the drape, for holding a solution therein, maintaining a barrier between the patient and doctor side while a surgical instrument extends therethrough, and expelling the solution onto the surgical instrument when inserted therethrough; and
    c) a collection bag attached to the patient side of the drape.

11. The surgical barrier of claim 10, further comprising adhesive means, located on the collection bag for releasably attaching the collection bag to a patient.

12. The surgical barrier of claim 10, wherein a periphery of the drape includes a patient adhering adhesive.

13. The surgical barrier of claim 10, wherein the reservoir means includes a pore for expelling the solution.

14. The surgical barrier of claim 10, wherein the reservoir means includes a refill means for refilling the reservoir with solution.

15. The surgical barrier of claim 14, wherein:
    the reservoir has a hollow walled ring shape that is formed circumfrentially around the valve means; and
    the hollow walled ring defines a cavity therebetween.

16. The surgical barrier of claim 15, wherein the reservoir means includes a valve means, located within the cavity adjacent the doctor side, for maintaining a barrier between the patient and doctor side while a surgical instrument extends therethrough.

17. The surgical barrier of claim 16, wherein the cavity includes a pore for expelling the solution onto the surgical instrument located within the cavity.

18. A method for performing a surgical procedure on a patient, the method comprising the steps of:
    a) providing a surgical barrier, said surgical barrier including;
       I) a drape, having a patient and doctor side;
       ii) a valve, located on the drape; and
       iii) a collection bag attached to the patient side of the drape;
    b) positioning the surgical barrier such that the valve is proximate to the portion of the patient upon which the surgical procedure is to be performed and such that collection bag will collect secretions from the patient during the surgical procedure;
    c) extending a surgical instrument through the valve means, the valve means maintaining a barrier between the patient and doctor side while the surgical instrument extends therethrough; and
    d) applying a solution to said surgical instrument from a reservoir means located adjacent the valve means.

19. The method of claim 18 wherein the step of providing a surgical barrier comprises adhesively attaching said surgical barrier to the patient and further comprising the step of adhesively attaching the collection bag to the patient for collecting fluids expelled from the patient into said collection means located on the patient side of the drape.

* * * * *